United States Patent
Yamaguchi

(10) Patent No.: US 9,857,467 B2
(45) Date of Patent: Jan. 2, 2018

(54) DETECTION DEVICE

(71) Applicant: FURUNO ELECTRIC CO., LTD., Nishinomiya, Hyogo (JP)

(72) Inventor: Takeharu Yamaguchi, Nishinomiya (JP)

(73) Assignee: FURUNO ELECTRIC COMPANY LIMITED, Nishinomiya (JP)

( * ) Notice: Subject to any disclaimer, the term of this patent is extended or adjusted under 35 U.S.C. 154(b) by 387 days.

(21) Appl. No.: 14/709,643

(22) Filed: May 12, 2015

(65) Prior Publication Data

US 2015/0346162 A1 Dec. 3, 2015

(30) Foreign Application Priority Data

May 28, 2014 (JP) ................................ 2014-110006

(51) Int. Cl.
*G01S 7/62* (2006.01)
*G01S 15/96* (2006.01)
*G01S 7/56* (2006.01)
*G01S 15/89* (2006.01)
*G01S 15/87* (2006.01)

(52) U.S. Cl.
CPC ............... *G01S 15/96* (2013.01); *G01S 7/56* (2013.01); *G01S 7/6263* (2013.01); *G01S 7/6281* (2013.01); *G01S 15/87* (2013.01); *G01S 15/89* (2013.01); *G01N 2291/044* (2013.01); *G01N 2291/102* (2013.01)

(58) Field of Classification Search
CPC ................................ G01S 15/89; G01S 7/6281
See application file for complete search history.

(56) References Cited

U.S. PATENT DOCUMENTS

| | | | | |
|---|---|---|---|---|
| 2012/0014220 A1* | 1/2012 | DePasqua | ........... | G01S 7/52004 367/88 |
| 2013/0215719 A1* | 8/2013 | Betts | ....................... | G01S 7/521 367/88 |

OTHER PUBLICATIONS

Furuno Electric Co., Ltd., "Furuno Operator's Manual (version FCV-10)", Nishinomiya, Japan, Sep. 1990.

* cited by examiner

*Primary Examiner* — Hovhannes Baghdasaryan
(74) *Attorney, Agent, or Firm* — Studebaker & Brackett PC

(57) ABSTRACT

It is an object to improve the visibility of a display screen on which a detected target is displayed. A detection device 1b is formed by a wave receiver disposed facing in a specific direction, and configured to periodically receive reflected waves corresponding to transmission wave transmitted from a wave transmitter, an echo train signal production component 8 configured to produce an echo train signal from each of the reflected waves, a distance from a starting point of the echo train signal corresponding to a distance from the wave transmitter, and an echo image signal production component 9 configured to produce an echo image signal based on each of the echo train signals in which each of the starting points is disposed at a specific reference point.

16 Claims, 12 Drawing Sheets

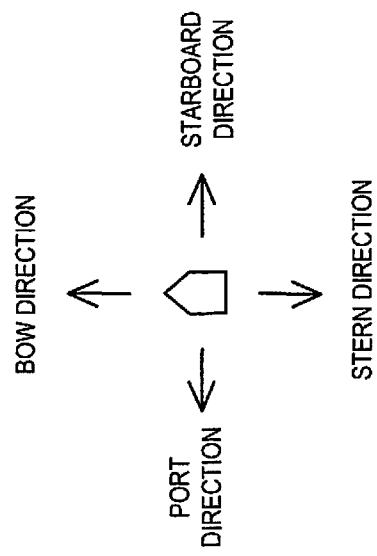
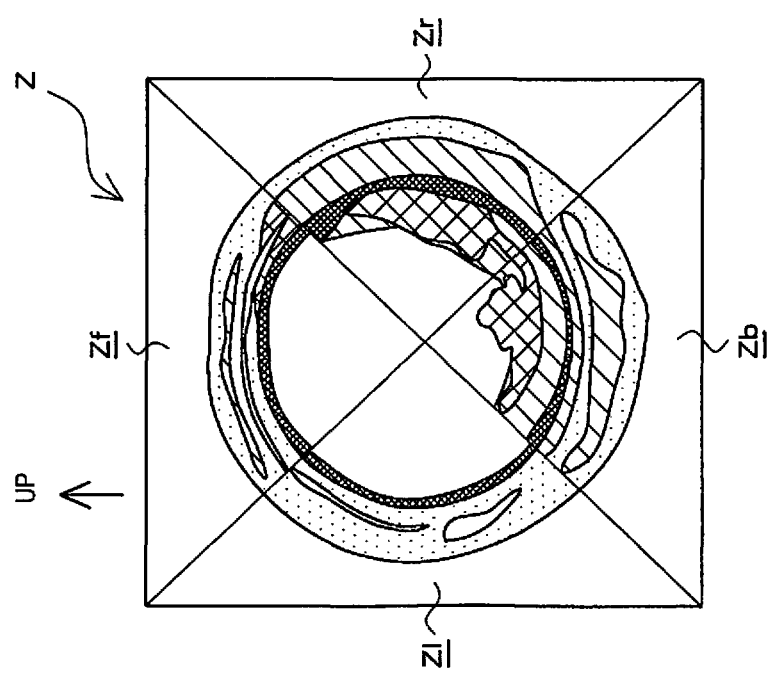
FIG. 6B
FIG. 6A

DETECTION DEVICE

CROSS-REFERENCE TO RELATED APPLICATIONS

This application claims priority to Japanese Patent Application No. 2014-110006 filed on May 28, 2014. The entire disclosure of Japanese Patent Application No. 2014-110006 is hereby incorporated herein by reference.

BACKGROUND

Field of the Invention

The present invention relates to a detection device equipped with a display device for displaying detected targets.

Background Information

There are known detection devices equipped with a display device for displaying detected targets on a display screen. For example, a display screen with a fish school detecting function (detection device) is disclosed on page 18 of Non-Patent Literature 1 (Furuno Electric Company, "Furuno Operator's Manual (version FCV-10)," Nishinomiya, Japan, September 1990). In this example, the display screen is split into three rectangular screens (left, middle, and right) that are taller than they are wide, with the undersea area in the port direction of the vessel displayed on the left screen, the undersea area in the vertically down direction on the middle screen, and the undersea area in the starboard direction on the right screen. This allows the user to ascertain the undersea state under the vessel in each direction.

SUMMARY

However, the display screen disclosed in the above-mentioned Non-Patent Literature 1 was unsatisfactory from the standpoint of visibility.

The present invention was conceived in an effort to solve the above problem, and it is an object thereof to improve the visibility of a display screen on which a detected target is displayed.

(1) To solve the above problem, the detection device pertaining to one aspect of the present invention comprises a wave receiver disposed facing in a specific direction, and configured to periodically receive reflected waves corresponding to transmission wave transmitted from a wave transmitter, an echo train signal production component configured to produce an echo train signal from each of the reflected waves, a distance from a starting point of the echo train signal corresponding to a distance from the wave transmitter, and an echo image signal production component configured to produce an echo image signal based on each of the echo train signals in which each of the starting points is disposed at a specific reference point.

(2) Preferably, the echo image signal production component is configured to produce the echo image signal in which the echo train signals extend radially in mutually different directions in a state in which the starting point of each of the echo train signals is disposed at the reference point.

(3) Preferably, the echo image signal production component is configured to output the produced echo image signal to a display device that is configured to display an echo image produced based on the echo image signal.

(4) More preferably, the detection device further comprises a plurality of the wave receivers, each reception beam formed by the wave receivers being oriented in mutually different directions, wherein the echo image signal production component is configured to produce an echo image signal for each direction based on the reflected waves received by the plurality of the wave receivers, and on the display device, echo image for each direction produced based on the echo image signal for each direction is displayed on a plurality of split screens obtained by splitting a display screen of the display device.

(5) More preferably, the reference point is provided in a center portion of the display screen, the split screens are provided as regions between first and second line segments that extend from the reference point toward an outside of the display screen, and positions of the split screens in the display screen correspond to directions of the reception beams respectively formed by the plurality of wave receivers, and echo train images produced based on echo train signals based on the reflected waves received by the respective wave receivers are displayed on the split screens corresponding to the respective wave receivers.

(6) More preferably, when the echo train signal is newly produced by the echo train signal production component, the echo image signal production component is configured to scroll the echo image displayed on the split screens at that point in time in a peripheral direction around the reference point from the first line segment side to the second line segment side, and configured to produce an echo image signal that displays at the first line segment side of the scrolled echo image an echo train image based on the newly produced echo train signal.

(7) Preferably, a third line segment that extends from the reference point toward the outside of the display screen is provided between the first line segment and the second line segment in each of the split screens, and when the echo train signal is newly produced by the echo train signal production component, in the echo image displayed on the split screens at that point in time, the echo image signal production component is configured to scroll the echo image between the first line segment and the third line segment in a peripheral direction around the reference point from the third line segment side to the first line segment side, configured to scroll the echo image between the second line segment and the third line segment in a peripheral direction around the reference point from the third line segment side to the second line segment side, and configured to produce an echo image signal that displays at the third line segment side of the scrolled echo image an echo train image based on the newly produced echo train signal.

(8) Preferably, the detection device is installed on a vessel and detects a target in the water, wherein the plurality of the wave receivers are attached to a hull bottom of the vessel, the reception beam of each wave receiver being oriented downward at an angle to a vertical direction.

(9) More preferably, the plurality of the wave receivers are attached to the hull bottom of the vessel, the reception beams of the wave receivers being oriented in a bow direction, a stern direction, a starboard direction, and a port direction of the vessel.

(10) More preferably, the detection device further comprises the wave transmitter, having a transmission beam oriented downward.

(11) Preferably, the detection device further comprises a plurality of the wave transmitters, each forming a transmission beam in a direction corresponding to the direction of the reception beam formed by each of the plurality of the wave receivers.

(12) More preferably, the detection device further comprises a plurality of wave transceivers provided as the plurality of the wave transmitters and the plurality of the wave receivers.

(13) Preferably, the detection device further comprises the display device.

The present invention improves the visibility of a display screen on which a detected target is displayed.

BRIEF DESCRIPTION OF THE DRAWINGS

Referring now to the attached drawings which form a part of this original disclosure:

FIG. 6A shows an example of the display screen displayed on the display device shown in FIG. 1;

FIG. 6B is a view from above of a vessel on which an underwater detector has been installed, and corresponds to the display screen shown in FIG. 6A;

DETAILED DESCRIPTION OF EMBODIMENTS

Figure 1:
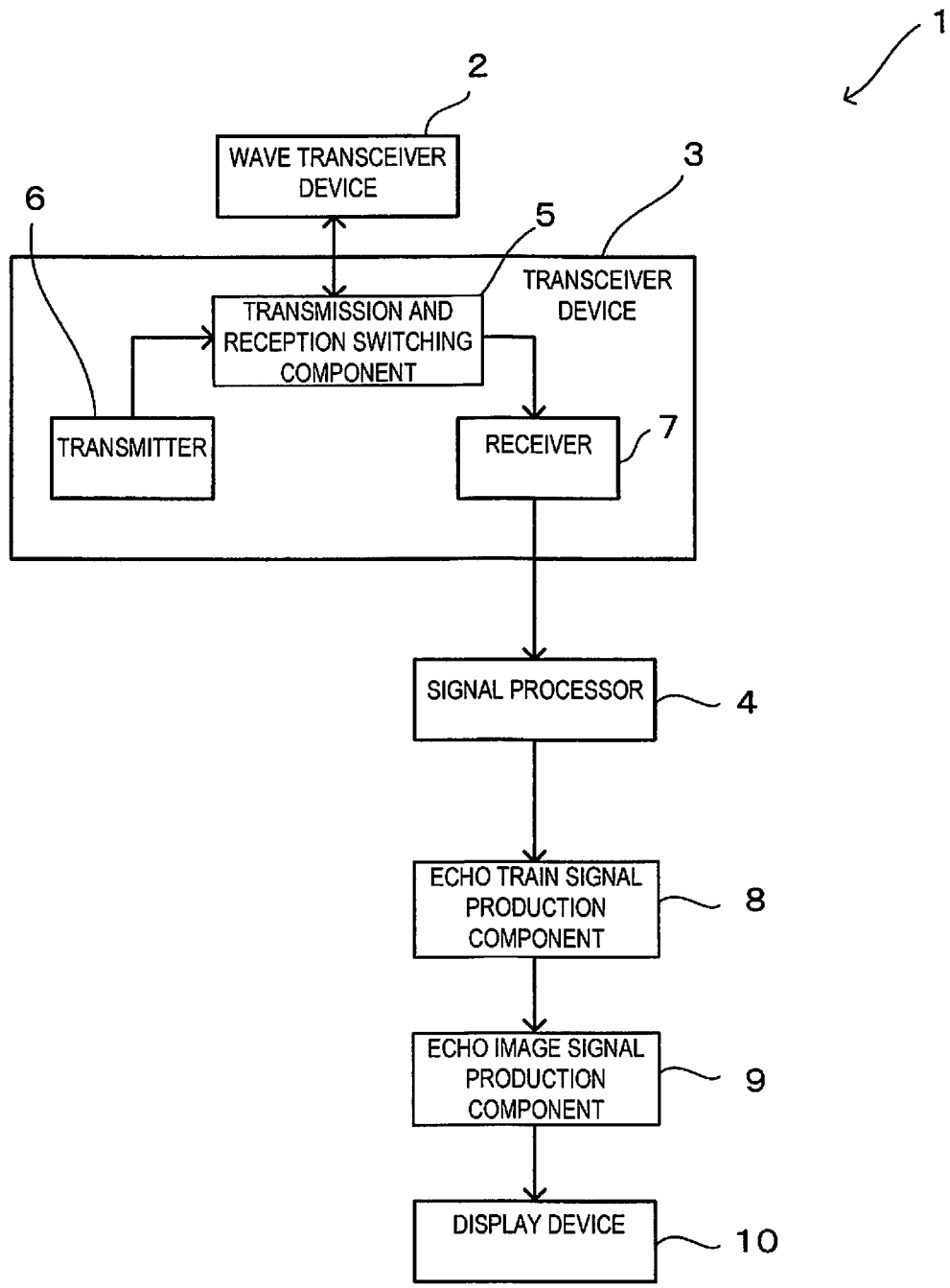
FIG. 1 is a block diagram of the configuration of an underwater detector pertaining to an embodiment of the present invention.

An embodiment of an underwater detector 1 will now be described through reference to the drawings, as an example of the detection device pertaining to the present invention. FIG. 1 is a block diagram of the configuration of the underwater detector 1 pertaining to an embodiment of the present invention. This underwater detector 1 is installed on a fishing boat or other such vessel, and is used to ascertain the shape of the seafloor, find schools of fish, and so forth.

Overall Configuration

As shown in FIG. 1, the underwater detector 1 comprises a wave transceiver device 2, a transceiver device 3, a signal processor 4, an echo train signal production component 8, an echo image signal production component 9, and a display device 10.

The wave transceiver device 2 is provided to the hull bottom so that the portions for transmitting and receiving ultrasonic waves is exposed underwater. The wave transceiver device 2 converts electrical signals into ultrasonic waves (transmission waves), sends these through the water, and converts received ultrasonic waves back into electrical signals.

Figure 2:
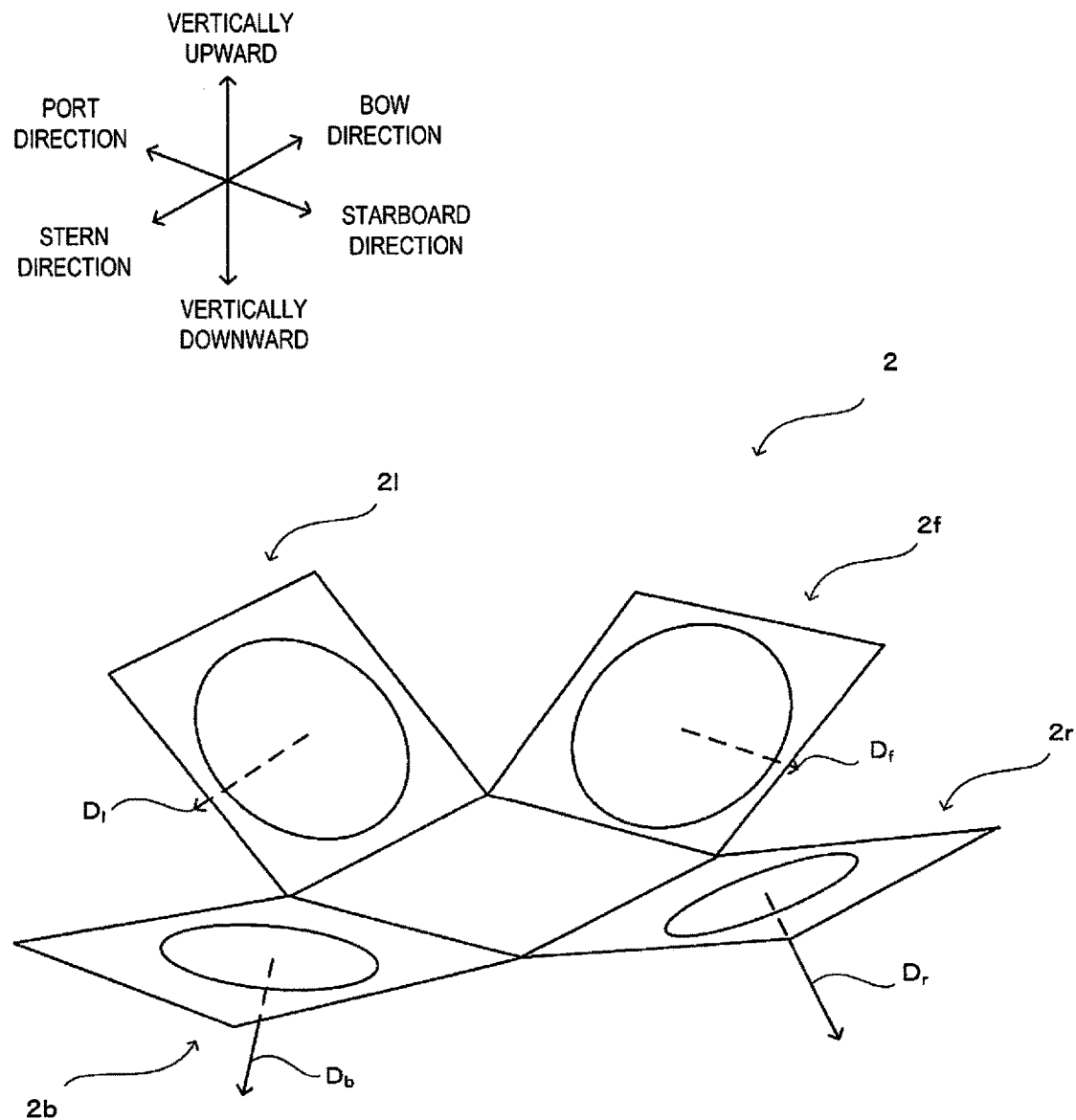
FIG. 2 is a simplified diagram of the layout of a plurality of wave transceivers within the wave transceiver device shown in FIG. 1.

FIG. 2 is a simplified diagram of the layout of a plurality of wave transceivers $2f$, $2b$, $2r$, and $2l$ within the wave transceiver device 2. The wave transceiver device 2 is made up of the four wave transceivers $2f$, $2b$, $2r$, and $2l$, or more specifically, a bow-side wave transceiver $2f$, a stern-side wave transceiver $2b$, a starboard-side wave transceiver $2r$, and a port-side wave transceiver $2l$. The wave transceivers $2f$, $2b$, $2r$, and $2l$ are constituted by ultrasonic vibrators. In FIG. 2, for the sake of convenience, of the wave transceivers $2f$, $2b$, $2r$, and $2l$, only the portion that transmits and receives ultrasonic waves (wave transmission and reception face) is shown in plan view.

The wave transceivers $2f$, $2b$, $2r$, and $2l$ are disposed so that the ultrasonic wave transmission and reception faces are facing downward and at an angle to the vertical direction in a state in which they have been attached to the hull bottom of the vessel and the vessel is floating in the sea. More specifically, as shown in FIG. 2, the bow-side wave transceiver $2f$ is disposed so that its transmission and reception face is facing in a direction $D_f$ that is inclined to the bow direction side from vertically downward. The stern-side wave transceiver $2b$ is disposed so that its transmission and reception face is facing in a direction $D_b$ that is inclined to the stern direction side from vertically downward. The starboard-side wave transceiver $2r$ is disposed so that its transmission and reception face is facing in a direction $D_r$ that is inclined to the starboard direction side from vertically downward. The port-side wave transceiver $2l$ is disposed so that its transmission and reception face is facing in a direction $D_l$ that is inclined to the port direction side from vertically downward. Consequently, the transmission beam and reception beam produced at the bow-side wave transceiver $2f$ are both formed in the direction $D_f$, the transmission beam and reception beam produced at the stern-side wave transceiver $2b$ are both formed in the direction $D_b$, the transmission beam and reception beam produced at the starboard-side wave transceiver $2r$ are both formed in the direction $D_r$, and the transmission beam and reception beam produced at the port-side wave transceiver $2l$ are both formed in the direction $D_l$. The wave transceivers $2f$, $2b$, $2r$, and $2l$ successively transmit ultrasonic waves at a specific timing (that is, at a specific period), and receive the reflected waves from the transmitted ultrasonic waves.

The transceiver device 3 comprises a transmission and reception switching component 5, a transmitter 6, and a receiver 7. The transmission and reception switching component 5 switches to a connection (first connection) in which a transmission signal is sent from the transmitter 6 to the wave transceiver device 2 during transmission. During reception, the transmission and reception switching component 5 switches to a connection (second connection) in which an electrical signal converted from an ultrasonic wave by the wave transceiver device 2 is sent from the wave transceiver device 2 to the receiver 7. The transmission and reception switching component 5 switches between the first connection and the second connection at a specific period. Consequently, the wave transceivers $2f$, $2b$, $2r$, and $2l$ successively transmit ultrasonic waves at a specific period, and receive the reflected waves corresponding to the transmitted ultrasonic waves at a specific period.

The transmitter 6 outputs transmission signals produced based on conditions set by the user, through the transmission and reception switching component 5 to the wave transceiver device 2.

The receiver 7 amplifies the signals received by the wave transceiver device 2, and subjects the amplified reception signals to A/D conversion. After this, the receiver 7 outputs the reception signals that have been converted into digital signals to the signal processor 4.

The signal processor 4 processes the reception signals outputted from the receiver 7, and outputs the processed reception signals to the echo train signal production component 8.

Figure 3:
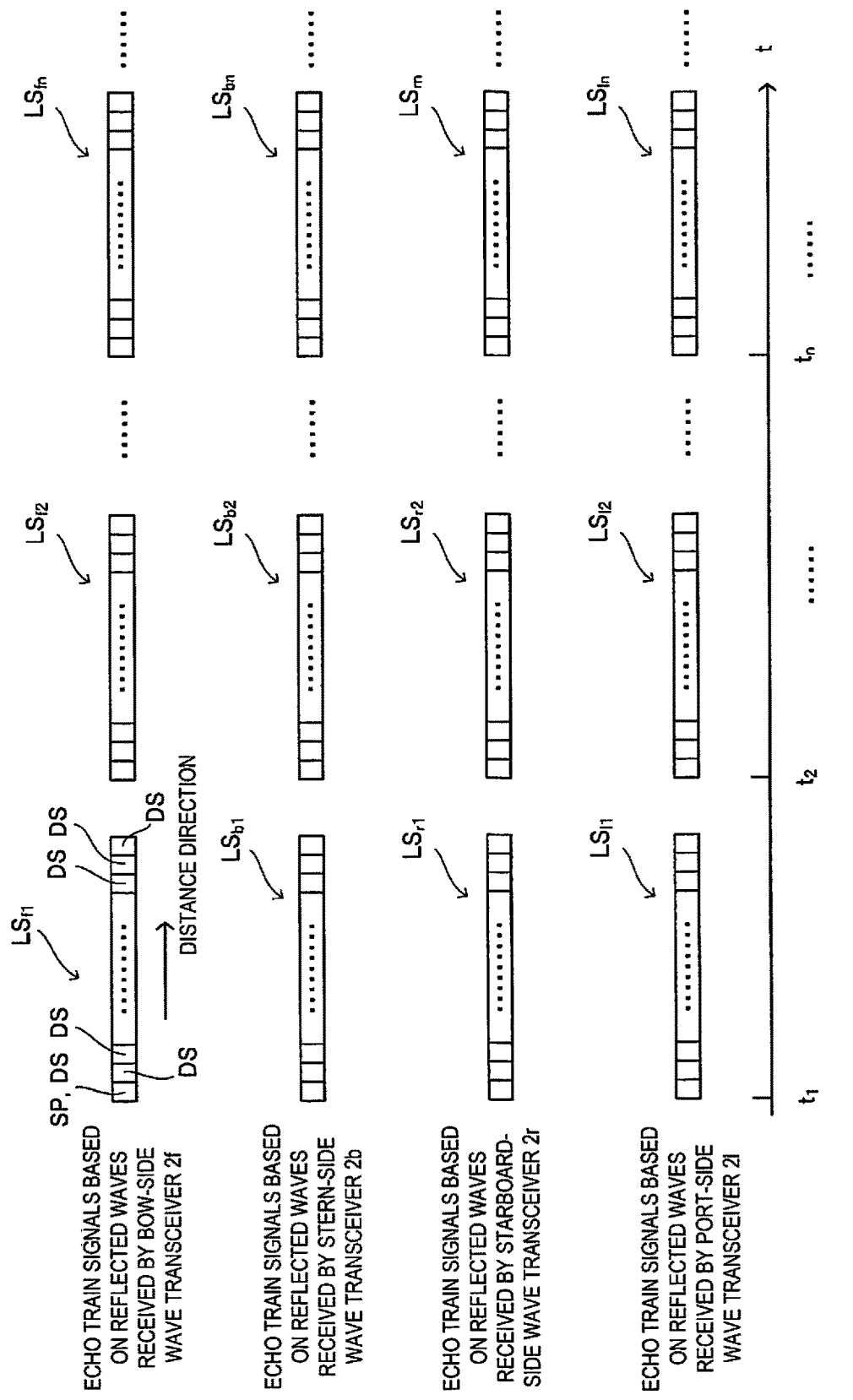
FIG. 3 is a simplified diagram illustrating echo train signals produced by the echo train signal production component shown in FIG. 1.

FIG. 3 is a simplified diagram illustrating echo train signals produced by the echo train signal production component 8. As discussed above, the wave transceivers 2f, 2b, 2r, and 2l successively transmit ultrasonic waves at a specific period, and receive the reflected waves corresponding to the transmitted ultrasonic waves at a specific period. The echo train signal production component 8 then processes, for each wave transceiver and each period, the reflected waves received at each period by the wave transceivers 2f, 2b, 2r, and 2l, and produces echo train signals for each wave transceiver and each period.

As shown in FIG. 3, each echo train signal LS is made up of dot signals DS arranged linearly (in a row). The dot signals DS are for example a signal corresponding to a dot picture DP serving as an image displayed by a single pixel on a display screen. Of the dot signals DS that make up each echo train signal LS, the dot signal DS formed based on the reflected wave that was first received is provided as a starting point SP for the echo train signal LS. The distance from the starting point SP of the dot signals DS constituting the echo train signal LS corresponds to the distance from the wave transceivers 2f, 2b, 2r, and 2l (that is, the distance from the vessel). A brightness level corresponding to the echo strength of the reflected wave is allocated to each of the dot signals DS, but in FIG. 3 the brightness levels allocated to the dot signals DS are not depicted.

The echo train signal production component 8, which will be described through reference to FIG. 3, produces echo train signals $LS_{f1}, LS_{f2}, \ldots, LS_{fn}, \ldots$ based on the reflected waves received at each period by the bow-side wave transceiver 2f. The echo train signal production component 8 also produces echo train signals $LS_{b1}, LS_{b2}, \ldots, LS_{bn}, \ldots$ based on the reflected waves received at each period by the stern-side wave transceiver 2b. The echo train signal production component 8 also produces echo train signals $LS_{r1}, LS_{r2}, \ldots, LS_{rn}, \ldots$ based on the reflected waves received at each period by the starboard-side wave transceiver 2r. The echo train signal production component 8 also produces echo train signals $LS_{l1}, LS_{l2}, \ldots, LS_{ln}, \ldots$ based on the reflected waves received at each period by the port-side wave transceiver 2l. The echo train signal production component 8 outputs the echo train signals LS as soon as they are produced to the echo image signal production component 9.

Figure 4:
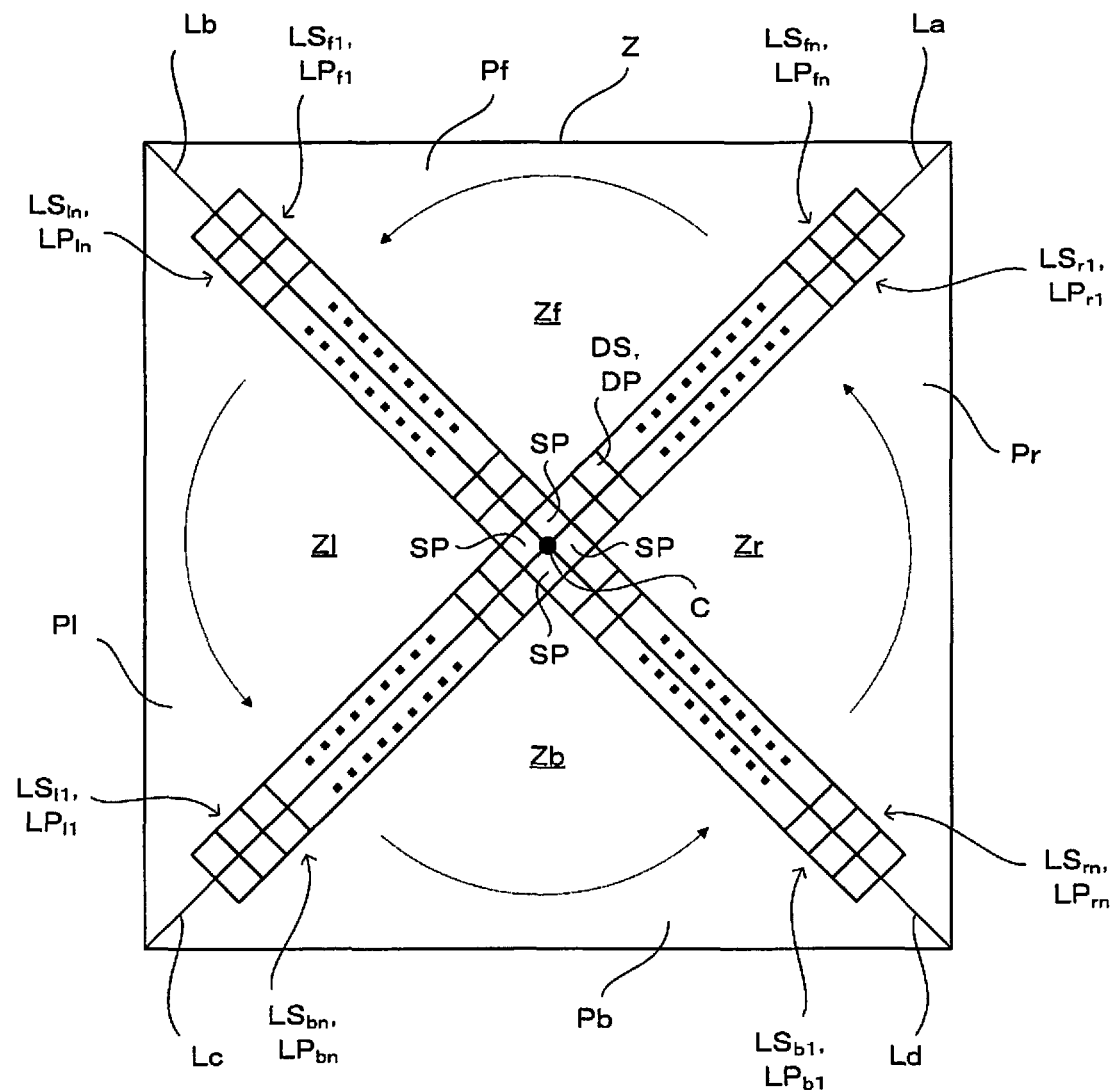
FIG. 4 is a simplified diagram illustrating the process by which echo image signals are produced by the echo image signal production component shown in FIG. 1.
Figure 5:
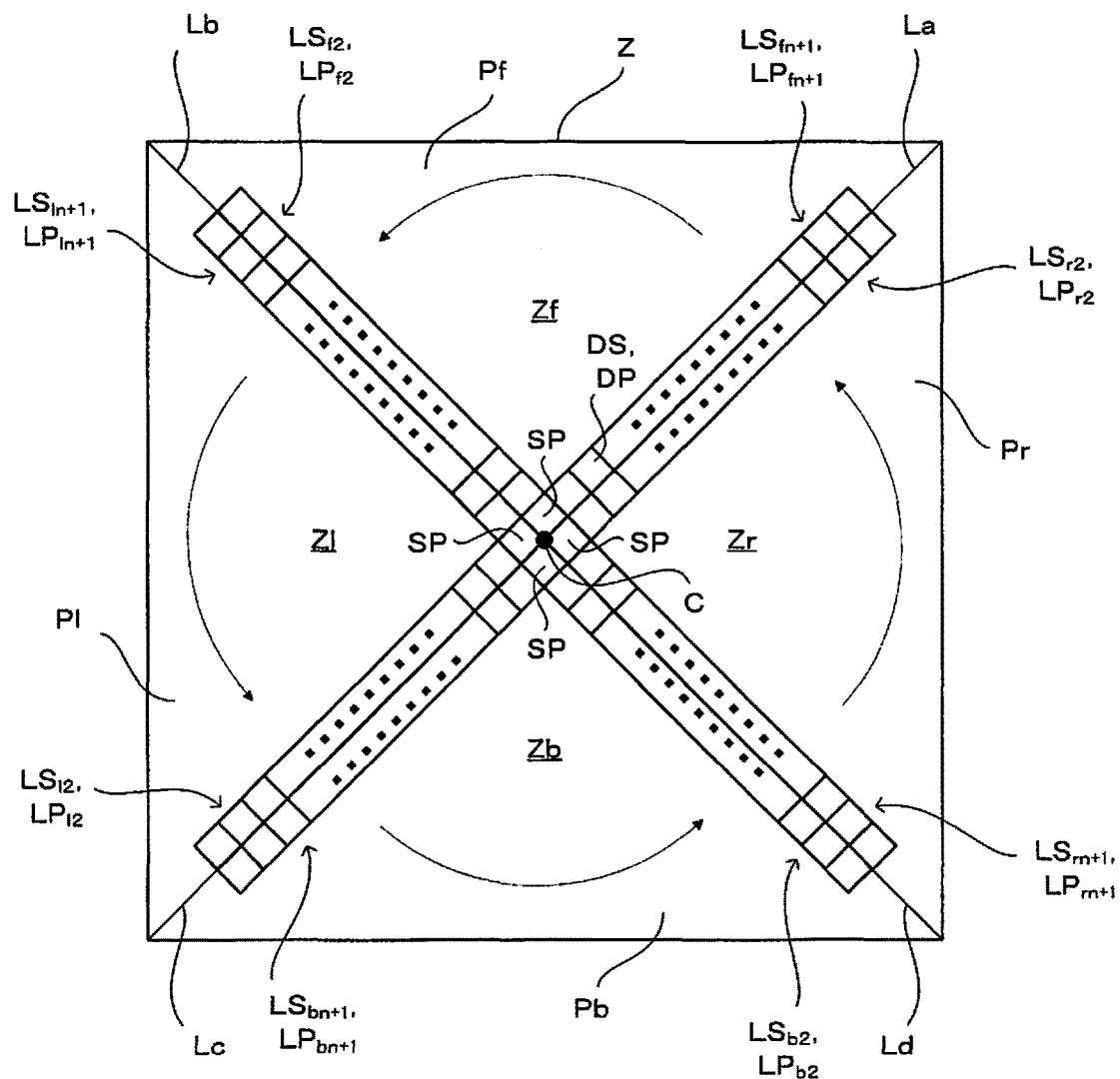
FIG. 5 is a simplified diagram illustrating the process by which echo image signals are produced by the echo image signal production component shown in FIG. 1.

FIGS. 4 and 5 are simplified diagrams illustrating the process in which echo image signals are produced by the echo image signal production component 9. The echo image signal production component 9 disposes the echo train signals LS produced by the echo train signal production component 8 based on a specific regularity (discussed below). The display of the brightness levels allocated to the dot signals DS is not depicted in FIGS. 4 and 5, just as in the above-mentioned FIG. 3.

Four line segments La, Lb, Lc, and Ld are displayed in the echo images produced based on the echo image signals produced by the echo image signal production component 9. The line segments La, Lb, Lc, and Ld are provided extending from the center point C of a display screen Z to the vertices of the display screen Z. The line segments La, Lb, Lc, and Ld are provided as first line segments and second line segments. More specifically, a line segment La is provided as a first line segment that demarcates a bow-side split screen Zf, and as a second line segment that demarcates a starboard-side split screen Zr. The line segment Lb is provided as a first line segment that demarcates a port-side split screen Zl, and as a second line segment that demarcates the bow-side split screen Zf. The line segment Lc is provided as a first line segment that demarcates a stern-side split screen Zb, and as a second line segment that demarcates the port-side split screen Zl. The line segment Ld is provided as a first line segment that demarcates the starboard-side split screen Zr, and as a second line segment that demarcates the stern-side split screen Zb. These line segments La, Lb, Lc, and Ld may be displayed on the display screen so that the user can recognize them, or may be provided as imaginary lines that are not displayed on the display screen.

As shown in FIG. 4, the display screen Z on which echo images are displayed is divided up into four split screens by the line segments La, Lb, Lc, and Ld. More specifically, the display screen Z is divided up into the bow-side split screen Zf, which is the region between the line segment La and the line segment Lb; the port-side split screen Zl, which is the region between the line segment Lb and the line segment Lc; the stern-side split screen Zb, which is the region between the line segment Lc and the line segment Ld; and the starboard-side split screen Zr, which is the region between the line segment Ld and the line segment La. An echo image Pf (echo image in each direction) that includes echo train images $LP_{f1}, LP_{f2}, \ldots$ based on the reflected waves received by the bow-side wave transceiver 2f is displayed on the bow-side split screen Zf. An echo image Pl (echo image in each direction) that includes echo train images $LP_{l1}, LP_{l2}, \ldots$ based on the reflected waves received by the port-side wave transceiver 2l is displayed on the port-side split screen Zl. An echo image Pb (echo image in each direction) that includes echo train images $LP_{b1}, LP_{b2}, \ldots$ based on the reflected waves received by the stern-side wave transceiver 2b is displayed on the stern-side split screen Zb. An echo image Pr (echo image in each direction) that includes echo train images $LP_{r1}, LP_{r2}, \ldots$ based on the reflected waves received by the starboard-side wave transceiver 2r is displayed on the starboard-side split screen Zr.

The echo images P are produced in the various split screens when the echo image signal production component 9 produces echo image signals in which the echo train signals LS are disposed as follows on the split screens Zf, Zl, Zb, and Zr. The echo image Pf displayed on the bow-side split screen Zf will now be described through reference to FIGS. 4 and 5, and then the echo images Pl, Pb, and Pr displayed on the port-side split screen Zl, the stern-side split screen Zb, and the starboard-side split screen Zr, respectively, will be described.

The echo image signal production component 9 produces the echo image Pf by producing echo image signals in which the echo train signals $LS_{f1}, LS_{f2}, \ldots$ extend in mutually different radial directions in a state in which they are disposed around the center point C, using as a reference point the starting points SP of the echo train signals $LS_{f1}, LS_{f2}, \ldots$. In this embodiment, the starting points SP of the echo train signals $LS_{f1}, LS_{f2}, \ldots$ coincide with the center point C. For the purpose of description, the positions of the starting points SP do not match up in FIGS. 4 and 5 (and more precisely, FIGS. 8 and 9 (discussed below)), but the positions of the starting points SP do match up on an actual display screen. The echo image signal production component 9 arranges the echo train signals $LS_{f1}$, $LS_{f2}$, . . . in the order in which they were produced and in the peripheral direction from the line segment Lb side toward the line segment La side. Specifically, on the bow-side split screen Zf, the echo train image displayed the most on the line segment Lb side (in FIG. 4, $LP_{f1}$) is the echo train image produced the longest ago out of the echo train images displayed on the bow-side split screen Zf at that point. Meanwhile, the echo train image displayed the most on the line segment La side (in FIG. 4, $LP_{fn}$) is the echo train image produced most recently out of the echo train images displayed on the bow-side split screen Zf at that point. The echo images Pl, Pb, and Pr are respectively produced in the port-side split screen Zl, the stern-side split screen Zb, and the starboard-side split screen Zr in the same way as with the bow-side split screen Zf.

When the echo image signal production component 9 receives a new echo train signal $LS_{fn+1}$ from the echo train signal production component 8 in a state in which the echo image Pf shown in FIG. 4 is displayed on the bow-side split screen Zf, the echo image Pf displayed on the bow-side split screen Zf at that point is scrolled counter-clockwise in FIG. 4 around the center point C. More specifically, the echo image signal production component 9 scrolls the echo image Pf by an amount equivalent to the line of echo train images LP. At this point of the echo image Pf displayed on the bow-side split screen Zf, the portion that is closest to the line segment Lb side ($LP_n$ in FIG. 4) disappears from the screen. At the same time, the newly produced echo train signal $LS_{fn+1}$ is displayed in the portion of the scrolled echo image Pf on the line segment La side. At this point the echo image signal production component 9 disposes the starting point SP of the echo train signal $LS_{fn+1}$ by using the center point C as a reference. More specifically, the echo image signal production component 9 disposes the echo train signal $LS_{fn+1}$ so that it extends radially, such that the starting point SP of the echo train signal $LS_{fn+1}$ coincides with the center point C. Consequently, the echo image Pf that includes the echo image signal $LP_{fn+1}$ produced by the newly produced echo train signal $LS_{fn+1}$ is displayed on the bow-side split screen Zf (see FIG. 5).

The echo image signal production component 9 produces echo image signals that serve as the basis for producing echo images in the same way as with the above-mentioned bow-side split screen Zf for the port-side split screen Zl, the stern-side split screen Zb, and the starboard-side split screen Zr as well.

More specifically, the echo image signal production component 9 scrolls the echo image Pl counter-clockwise upon receipt of a new echo train signal $LS_{ln+1}$. At the same time, a newly produced echo train image $LP_{ln+1}$ is displayed in the portion of the scrolled echo image Pl on the line segment Lb side (see FIG. 5). The echo image signal production component 9 also scrolls the echo image Pb counter-clockwise upon receipt of a new echo train signal $LS_{bn+1}$. At the same time, a newly produced echo train image $LP_{bn+1}$ is displayed in the portion of the scrolled echo image Pb on the line segment Lc side (see FIG. 5). The echo image signal production component 9 also scrolls the echo image Pr counter-clockwise upon receipt of a new echo train signal $LS_{rn+1}$. At the same time, a newly produced echo train image $LP_{rn+1}$ is displayed in the portion of the scrolled echo image Pr on the line segment Ld side (see FIG. 5).

The echo image signal production component 9 repeats the above operation every time a new echo train signal is produced, and the echo image displayed at that point is updated to an echo image that includes the newly produced echo train image.

The echo image Pf displayed on the bow-side split screen Zf is produced as above. Specifically, on the bow-side split screen Zf, the echo image Pf is scrolled counter-clockwise around the center point C from the line segment La side, and is displayed in the portion (line segment La side) on the opposite direction side from the direction in which the newly produced echo train image is scrolled. Consequently, with the echo image Pf displayed on the bow-side split screen Zf, the echo train image displayed the most on the line segment La side becomes the echo train image based on the most recent reflected wave received by the bow-side wave transceiver 2f. Similarly, with the port-side split screen Zl, the echo train image displayed the most on the line segment Lb side becomes the echo train image based on the most recent reflected wave received by the port-side wave transceiver 2l. Also, with the stern-side split screen Zb, the echo train image displayed the most on the line segment Lc side becomes the echo train image based on the most recent reflected wave received by the stern-side wave transceiver 2b. Also, with the starboard-side split screen Zr, the echo train image displayed the most on the line segment Ld side becomes the echo train image based on the most recent reflected wave received by the starboard-side wave transceiver 2r.

FIG. 6A shows an example of the display screen Z displayed on the display device 10. FIG. 6B is a view from above of a vessel, and corresponds to the display screen Z shown in FIG. 6A. The display screen Z of the display device 10 is formed in a square shape in this example, and when the display device 10 has been installed in the vessel, the direction of the arrow labeled "up" in FIG. 6 is upward. The display device 10 is installed, for example, in a vessel so that the display screen Z is facing the user when the user is looking toward the bow.

A brightness level corresponding to echo strength is allocated to the various dot images that make up the echo images displayed on the display device 10. More specifically, as the brightness level changes from higher to lower, the coloring of the dot images gradually changes from red to orange, yellow, green, light blue, and dark blue, in that order. In FIG. 6, as the brightness level changes from higher to lower, the density of the hatching gradually thins out. The user can look at this echo image to recognize the state of the seafloor, whether there are any schools of fish, and so forth in each of the directions under the vessel (the bow direction, the port direction, the stern direction, and the starboard direction). The densest cross-hatching in FIG. 6A is attributable to the seafloor, and the hatching that is closer to the display screen center side than this dense cross-hatching is attributable to a prominence on the seafloor, a rock that sticks up from the seafloor, or the like.

As shown in FIG. 6, the positions of the various split screens of the display screen Z (the bow-side split screen Zf, the port-side split screen Zl, the stern-side split screen Zb, and the starboard-side split screen Zr) correspond to directions using the vessel as a reference (the bow direction, the port direction, the stern direction, and the starboard direction). This allows the user to easily and visually ascertain the direction from which an echo image displayed on the screen has arrived.

Effect

As discussed above, with the underwater detector 1 pertaining to this embodiment, the echo strength at various points underwater can be confirmed, so the state of an underwater target (seafloor state, presence of schools of fish, etc.) can be gathered from this echo strength.

Also, with the underwater detector 1, the starting points SP of the echo train signals LS are disposed using a specific reference point (the center point C of the display screen Z in this embodiment) that lies within the display screen Z. More specifically, in this embodiment the starting points SP of the echo train signals LS coincide with the center point C.

For example, with the display screen disclosed on page 18 of Non-Patent Literature 1, the starting points of the echo train images (the images in a single row on this display screen) move in parallel within the display screen. This starting point position corresponds to the position of the vessel. Thus, with Non-Patent Literature 1, because the position (starting point position) that serves as a reference when the user ascertains echo train images is moving over time, this approach cannot be considered satisfactory in terms of visibility.

By contrast, with this embodiment, as discussed above, the starting points SP of the echo train images LP (that is, dot images displaying the echo strength of reflected waves from the point of ground closest to the vessel out of all the echo train images LP) can be collected into a single place on the screen (the center portion of the display screen Z in this embodiment), so the relation between echo train images and the position of the vessel can be easily grasped visually.

Therefore, with the underwater detector 1, the visibility of the display screen Z on which a detected target is displayed can be improved.

Also, with the underwater detector 1, since the echo train images LP are disposed so as to extend in mutually different directions on the display screen Z, the echo train images LP do not overlap each other on the display screen Z, which means the echo train images LP can be displayed more efficiently.

Also, with the underwater detector 1, the echo images displayed on the display screen Z are scrolled in the peripheral direction around the center point C. That is, with the underwater detector 1, the echo history can be displayed on the same screen. The user can ascertain the shape of underwater structures (the seafloor, etc.) by checking this echo history.

Also, with the underwater detector 1, the echo images Pf, Pl, Pb, and Pr based on the reflected waves received by the wave transceivers 2f, 2b, 2r, and 2l that face in mutually different directions are displayed on the corresponding split screens Zf, Zl, Zb, and Zr. Consequently, the directions using the vessel as a reference (the bow direction, the stern direction, the starboard direction, and the port direction) can be more easily associated with the echo train images LP disposed on the display screen Z using a reference point as a reference. Therefore, the visibility of the display screen Z can be further improved.

Also, with the underwater detector 1, the reference point C is disposed in the center portion of the display screen Z, and the echo images Pf, Pl, Pb, and Pr are displayed on the split screens Zf, Zl, Zb, and Zr, which spread out toward the outside of the display screen Z. Consequently, the position of an underwater target in relation to the vessel as displayed by the reference point C can be easily and intuitively grasped.

Also, with the underwater detector 1, the echo images Pf, Pl, Pb, and Pr displayed on the split screens Zf, Zl, Zb, and Zr, which are demarcated by the first line segments La, Lb, Lc, and Ld and the second line segments Lb, Lc, Ld, and La, are scrolled from the side of the first line segments La, Lb, Lc, and Ld in the peripheral direction toward the side with the second line segments Lb, Lc, Ld, and La. This allows an echo history to be displayed over a relatively wide range.

Also, with the underwater detector 1, the wave transceiver devices 2 are attached to the hull bottom so that the reception beams of the wave transceivers 2f, 2b, 2r, and 2l face downward at an angle to vertically downward. This allows an underwater target beneath the vessel to be properly detected.

Also, with the underwater detector 1, the reception beams of the wave transceivers 2f, 2b, 2r, and 2l are respectively oriented in the bow direction, the stern direction, the starboard direction, and the port direction. This allows targets under the vessel to be detected without missing any.

Also, with the underwater detector 1, the directions of the transmission beams produced by the wave transceivers 2f, 2b, 2r, and 2l are made to correspond to the directions of the reception beams. This allows the echo strength to be found more accurately for each point under water.

Also, with the underwater detector 1, the plurality of wave transceivers 2f, 2b, 2r, and 2l are provided as a plurality of wave receivers and a plurality of wave transmitters. This means that the wave receivers and wave transmitters can be shared, which simplifies the configuration of the wave transceiver device 2.

MODIFICATION EXAMPLES

An embodiment of the present invention was described above, but the present invention is not limited to or by this, and various modifications are possible without departing from the gist of the present invention.

Figure 7:
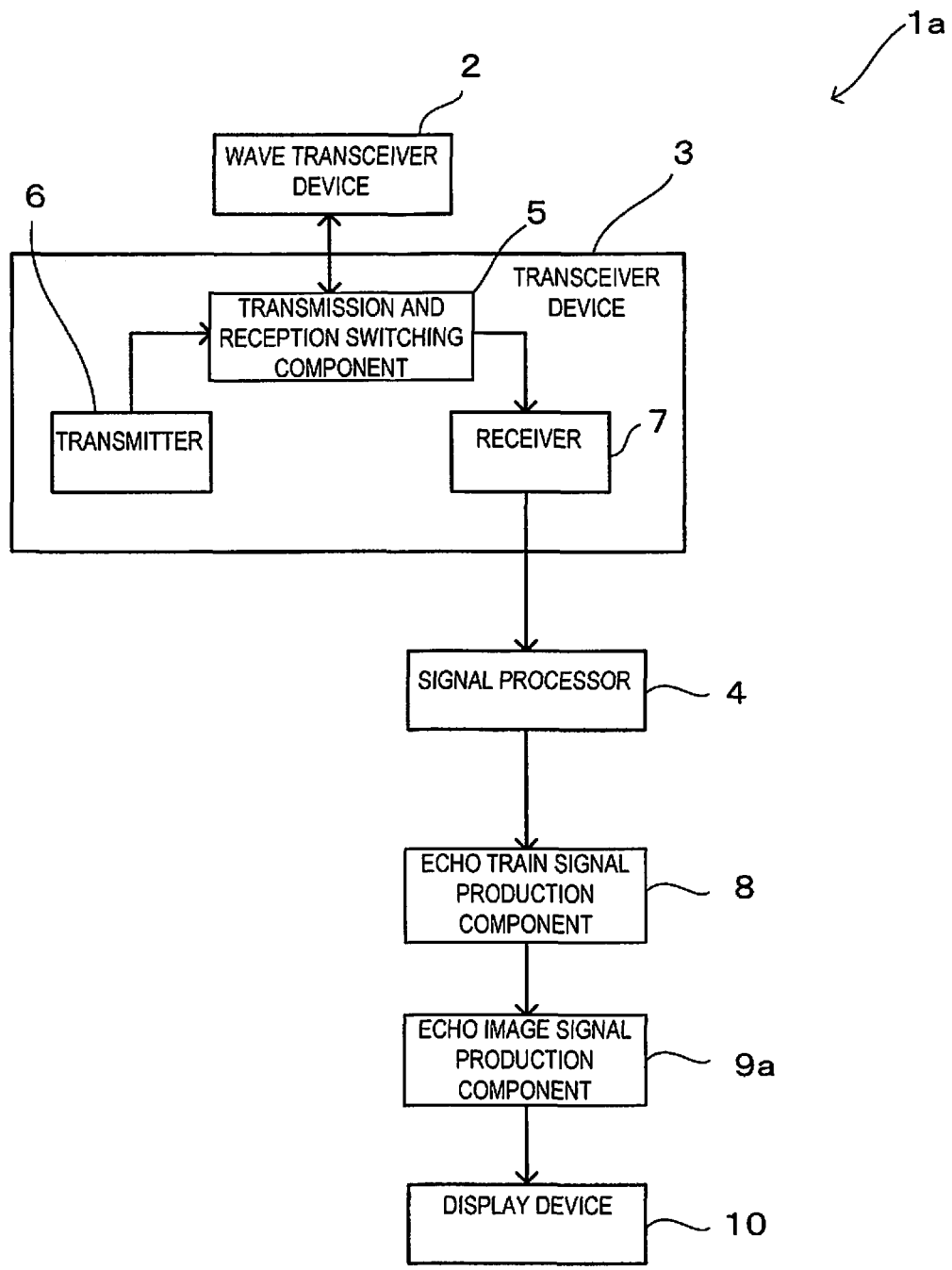
FIG. 7 is a block diagram of the configuration of an underwater detector pertaining to a modification example of the present invention.

(1) FIG. 7 is a block diagram of the configuration of an underwater detector 1a pertaining to a modification example. The underwater detector 1a pertaining to this modification example differs from the underwater detector 1 pertaining to the above embodiment in the configuration of the echo image signal production component. The following description will focus on the portion that is different from the above embodiment, and the other portions will not be described again.

Figure 8:
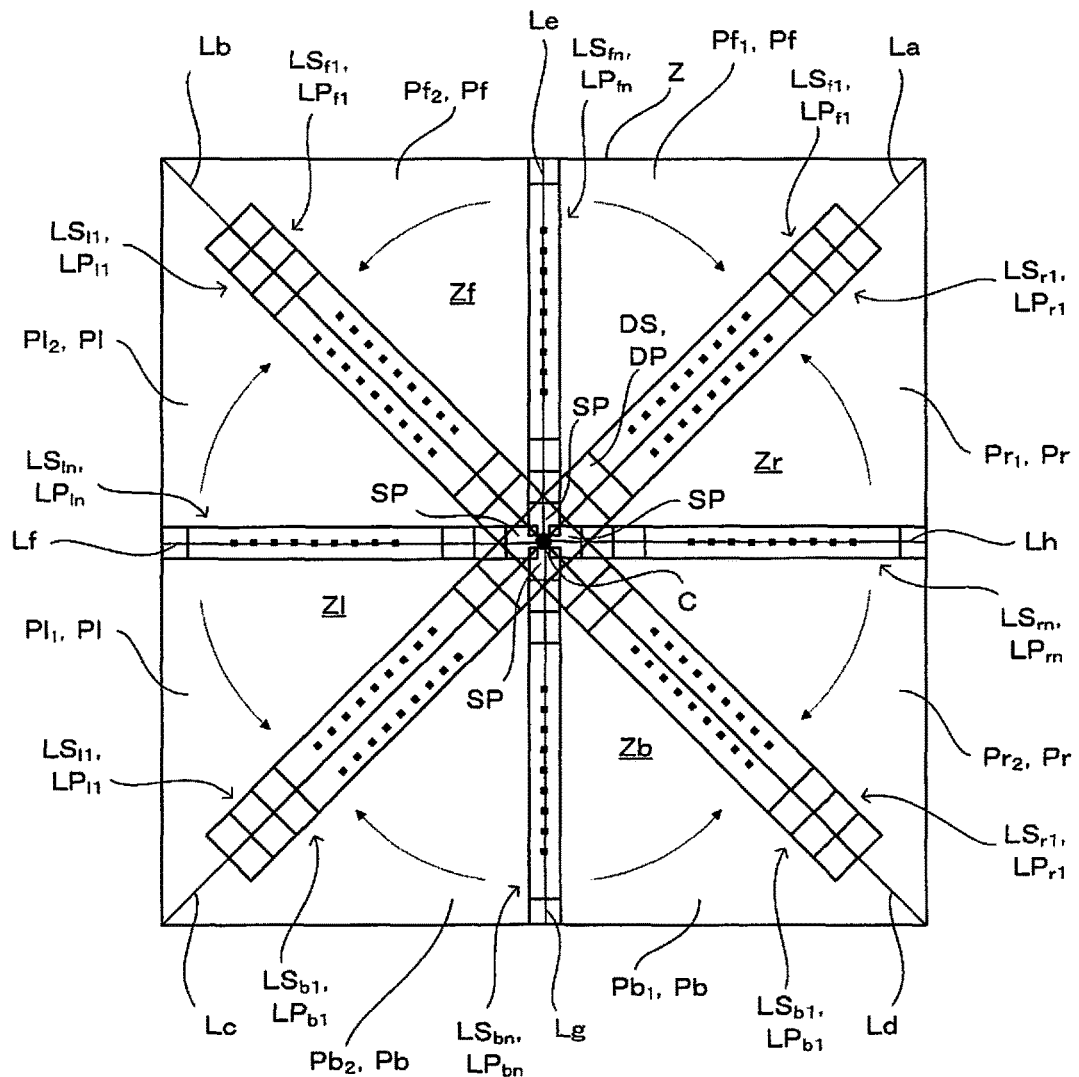
FIG. 8 is a simplified diagram illustrating the process by which echo image signals are produced by the echo image signal production component shown in FIG. 7, and corresponds to FIG. 4.
Figure 9:
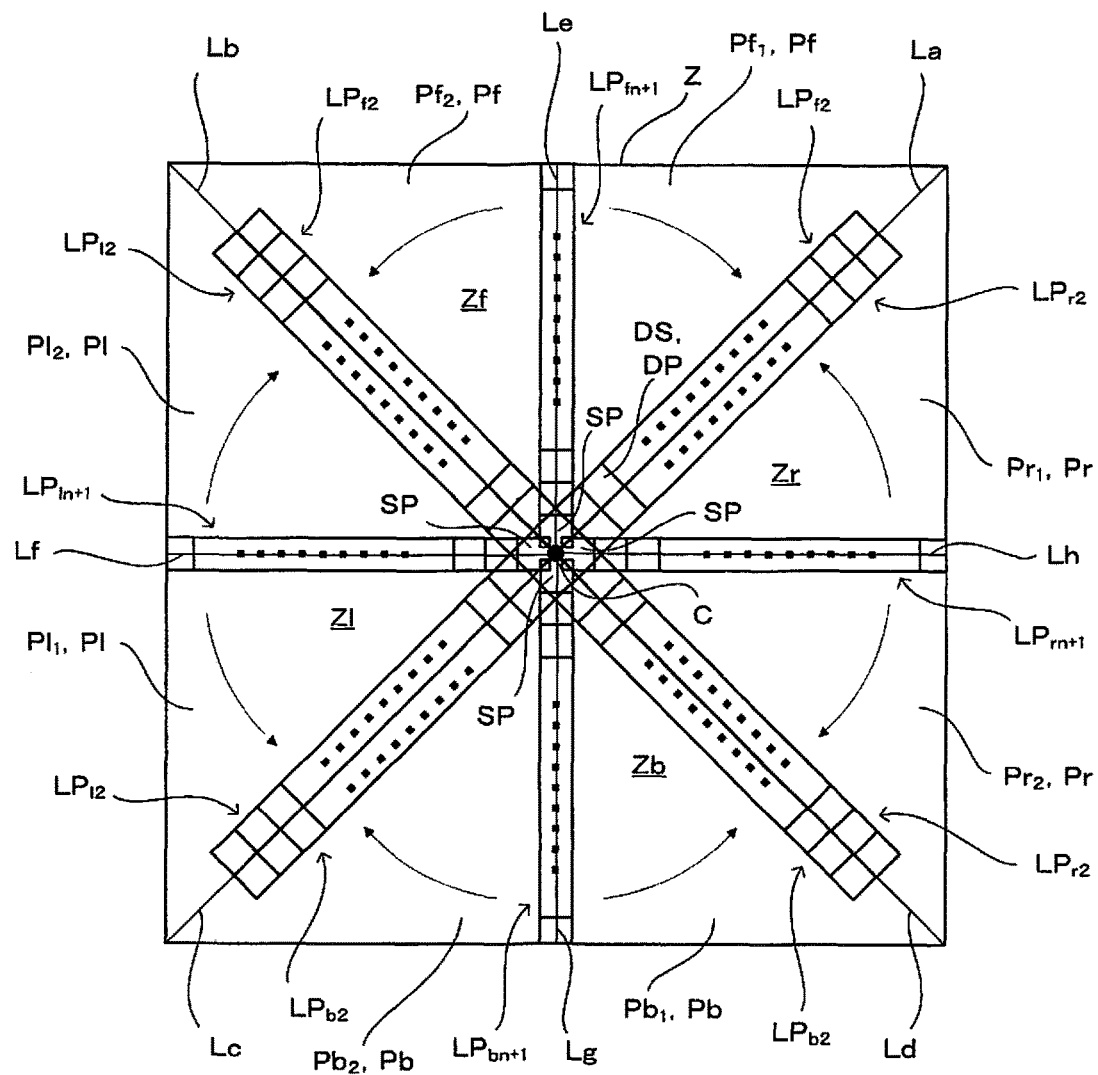
FIG. 9 is a simplified diagram illustrating the process by which echo image signals are produced by the echo image signal production component shown in FIG. 7, and corresponds to FIG. 5.

FIGS. 8 and 9 are simplified diagrams illustrating the process by which echo image signals are produced by echo image signal production component 9a pertaining to this modification example, and correspond to FIGS. 4 and 5. The echo image signal production component 9a is similar to the echo image signal production component 9 in the above embodiment in that the echo train signal produced by the echo train signal production component 8 are disposed based on a specific regularity within the display screen Z, to produce echo image signals that serve as the basis for producing echo images.

In addition to the four line segments La, Lb, Lc, and Ld, four line segments Le, Lf, Lg, and Lh (third line segments) are displayed in the echo images displayed on the display device 10 pertaining to this modification example. The line segments Le, Lf, Lg, and Lh are provided extending from the center point C in the echo image to the center points of the edges constituting the display screen Z. The line segments Le, Lf, Lg, and Lh are similar to the line segments La, Lb, Lc, and Ld in that they may be displayed on the display screen so that they can be recognized by the user, or may be provided as imaginary lines that are not displayed on the display screen.

The echo image signal production component 9a produces echo images P in the split screens Zf, Zl, Zb, and Zr by producing echo image signals in which the echo train signals LS are disposed as follows on the split screens Zf, Zl, Zb, and Zr. Below, the echo image Pf displayed on the bow-side split screen Zf will be described through reference to FIGS. 8 and 9, and then the echo images Pl, Pb, and Pr respectively displayed on then port-side split screen Zl, the stern-side split screen Zb, and the starboard-side split screen Zr will be described.

The echo image signal production component 9a is similar to the echo image signal production component 9 in the above embodiment in that in a state in which the starting points SP of the echo train signals $LS_{f1}$, $LS_{f2}$, . . . are disposed as reference points around the center point C, echo image signals are produced in which the echo train signals $LS_{f1}$, $LS_{f2}$, . . . extend radially in mutually different directions, thereby producing the echo image Pf. The echo image signal production component 9a then arranges the successively produced echo train signals $LS_{f1}$, $LS_{f2}$, . . . in the peripheral direction from the line segment Le side toward the line segment La side, and arranges them in the peripheral direction from the line segment Le side toward the line segment Lb side. Consequently, the echo image Pf displayed on the bow-side split screen Zf becomes an image in linear symmetry in which the line segment Le is the axis of symmetry.

On the bow-side split screen Zf, the echo train image that is displayed the furthest to the line segment La side and the echo train image that is displayed the furthest to the line segment Lb side ($LP_{f1}$ in FIG. 8) are echo train images produced the longest ago out of the echo train images displayed on the bow-side split screen Zf at that point in time. Meanwhile, the echo train image displayed on the line segment Le ($LP_{fn}$ in FIG. 4) is the echo train image produced most recently out of the echo train images displayed on the bow-side split screen Zf at that point. The echo images Pl, Pb, and Pr are respectively produced on the port-side split screen Zl, the stern-side split screen Zb, and the starboard-side split screen Zr in the same manner as on the bow-side split screen Zf.

When the echo image signal production component 9a receives a new echo train signal $LS_{fn+1}$ from the echo train signal production component 8 in a state in which the echo image shown in FIG. 8 is displayed on the bow-side split screen Zf, the echo image $Pf_1$ between the line segment La and the line segment Le out of the echo image Pf displayed on the bow-side split screen Zf at that point is scrolled clockwise in FIG. 8, and the echo image $Pf_2$ between the line segment Lb and the line segment Le is scrolled counterclockwise. At this point, the portion of the echo image $Pf_1$ that is furthest to the line segment La side, that is, the echo train image ($LP_{f1}$ in FIG. 8) produced the longest ago out of the echo train images included in the echo image $Pf_1$, disappears from the screen. Similarly, the portion of the echo image $Pf_2$ that is furthest to the line segment Lb side, that is, the echo train image ($LP_{f1}$ in FIG. 8) produced the longest ago out of the echo train images included in the echo image $Pf_2$, disappears from the screen. Simultaneously with this, the newly produced echo train image $LP_{fn+1}$ is displayed on the line segment Le. At this point, the echo image signal production component 9a is similar to the echo image signal production component 9 in the above embodiment in that it disposes the starting point SP of the echo train signal $LS_{fn+1}$ so as to coincide with the center point C serving as a reference point, and disposes the echo train signal $LS_{fn+1}$ so as to extend radially. Consequently, the echo image Pf including the echo train image $LP_{fn+1}$ produced by the newly produced echo train signal $LS_{fn+1}$ is displayed on the bow-side split screen Zf (see FIG. 9).

The echo image signal production component 9a then produces echo image signals that will serve as the basis for producing echo images, in the same way as with the bow-side split screen Zf discussed above, for the port-side split screen Zl, the stern-side split screen Zb, and the starboard-side split screen Zr.

Figures 10A, 10B:
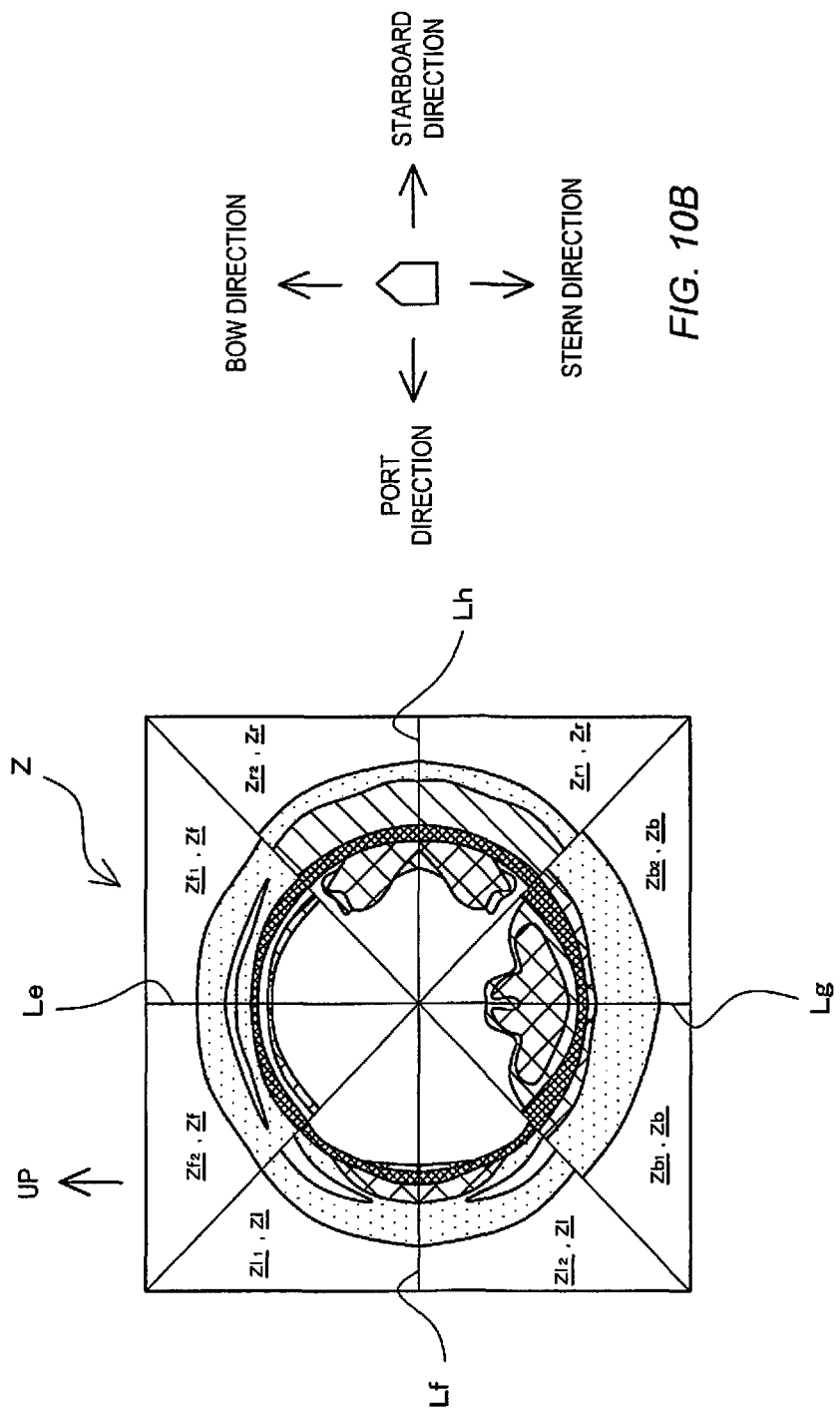
FIG. 10A shows an example of the display screen displayed on the display device shown in FIG. 7.
FIG. 10B is a view from above of a vessel on which an underwater detector has been installed, and corresponds to the display screen shown in FIG. 10A.

FIG. 10A is an example of the display screen Z displayed on the display device 10. FIG. 10B is a view of a vessel from above, and corresponds to the display screen Z shown in FIG. 10A. In this modification example, unlike in the above embodiment, the echo train image produced most recently is displayed on the line segments Le, Lf, Lg, and Lh (third line segments). Consequently, as shown in FIG. 10, the echo train image produced most recently can be displayed corresponding to the bow direction, the port direction, the stern direction, and the starboard direction. As a result, although the number of echo histories displayed on the display screen Z is fewer than in the above embodiment, the direction of the most recent echo train image in the display screen Z can be made to correspond to directions in relation to the vessel. This allows the orientation of the most recent echo train image to be easily grasped.

(2) In the above embodiment and the above modification example, the four wave transceivers 2f, 2b, 2r, and 2l were provided to the wave transceiver device 2, but this is not the only option, and three or fewer, or five or more, wave transceivers may be provided. Also, in the above embodiment and the above modification example, the four wave transceivers 2f, 2b, 2r, and 2l were disposed respectively facing in the bow direction, the stern direction, the starboard direction, and the port direction, but this is not the only option, and they may face in some other direction instead.

(3) In the above embodiment and the above modification examples, an underwater detector was given as an example of an application of the present invention, but this is not the only option, and the present invention can also be applied to some other type of detection device, such as a radar device.

Figure 11:
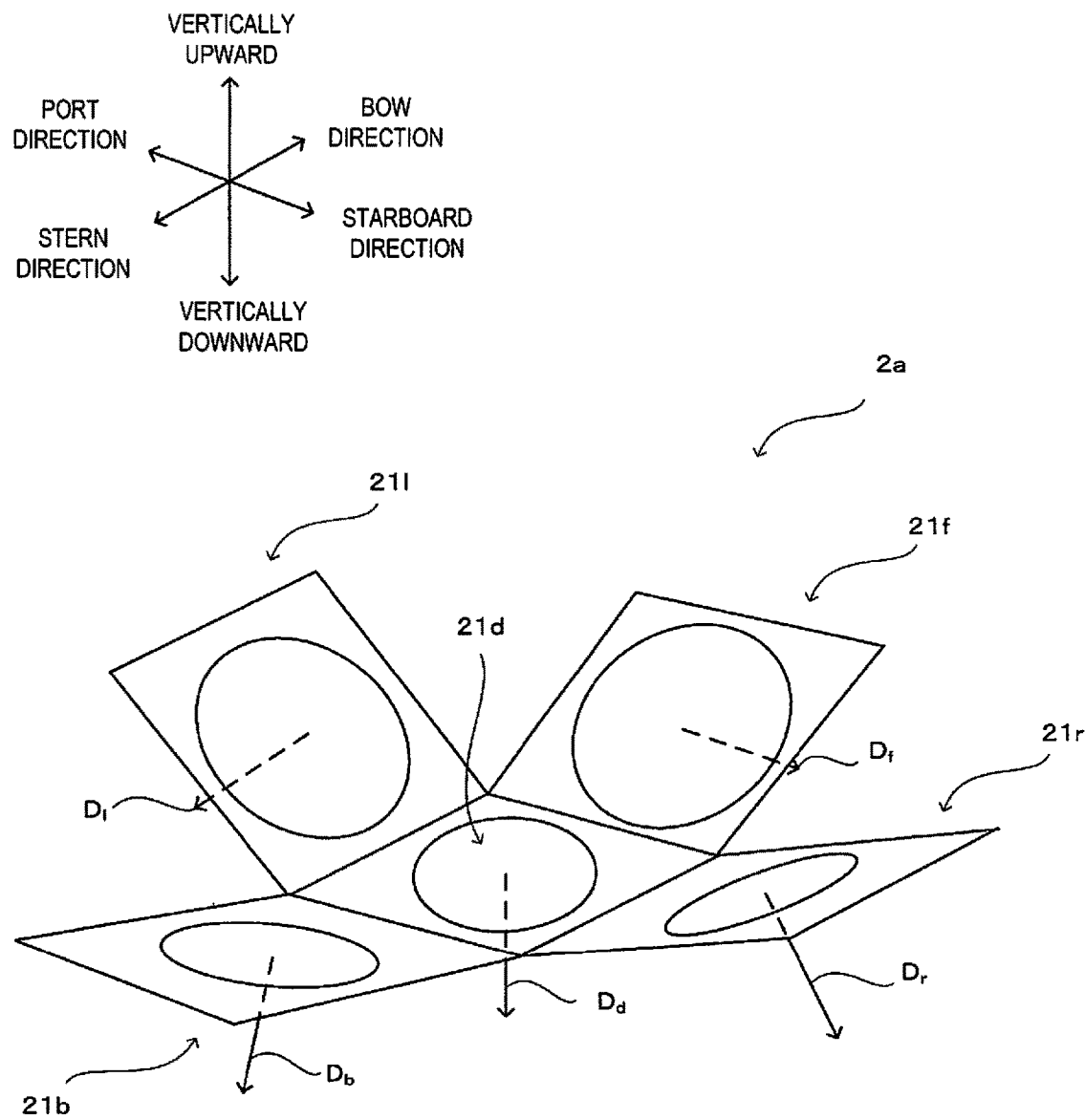
FIG. 11 is a simplified diagram of the configuration of the wave transceivers of an underwater detector pertaining to a modification example.

(4) FIG. 11 is a simplified diagram of the layout of a plurality of wave receivers 21f, 21b, 21r, and 21l and a wave transmitter 21d within a wave transceiver device 2a of the underwater detector pertaining to a modification example. As shown in FIG. 11, the wave transceiver device 2a pertaining to this modification example has the one wave transmitter 21d and the four wave receivers 21f, 21b, 21r, and 21l.

The wave transmitter 21d is configured to transmit ultrasonic waves. The wave transmitter 21d is disposed so that the ultrasonic wave transmission face is pointed vertically downward in a state in which the wave transmitter 21d is attached to the hull bottom of a vessel (ship) and the vessel is afloat. Consequently, the transmission beam produced by the wave transmitter 21d is formed so as to be oriented vertically downward (the Dd direction). The transmission beam produced by the wave transmitter 21d is wider than the reception beams formed by the wave receivers 21f, 21b, 21r, and 21l.

The four wave receivers 21f, 21b, 21r, and 21l are configured to receive ultrasonic waves. The four wave receivers 21f, 21b, 21r, and 21l are a bow-side wave receiver 21f, a stern-side wave receiver 21b, a starboard-side wave receiver 21r, and a port-side wave receiver 21l. The wave receivers 21f, 21b, 21r, and 21l are arranged the same as the wave transceivers 2f, 2b, 2r, and 2l in the above embodiment. Specifically, the bow-side wave receiver 21f is disposed so that its wave reception face is pointed in a De direction that is inclined to the bow direction side from vertically downward. The stern-side wave receiver 21b is disposed so that its wave reception face is pointed in a $D_b$ direction that is inclined to the stern direction side from vertically downward. The starboard-side wave receiver 21r is disposed so that its wave reception face is pointed in a $D_r$ direction that is inclined to the starboard direction side from vertically downward. The port-side wave receiver 21*l* is disposed so that its wave reception face is pointed in a $D_l$ direction that is inclined to the port direction side from vertically downward.

As discussed above, in this modification example, one wave transmitter 21*d* is provided. Consequently, there is no interference between ultrasonic waves from different wave transmitters, as can happen when ultrasonic waves are transmitted from a plurality of wave transmitters, so this prevents the transmission beam from having a distorted shape.

Also, in this modification example, since the transmission beam is wider than the reception beams, a relatively wide area can be searched under the vessel. Furthermore, since the wave transmission face of the wave transmitter 21*d* in this modification example is pointed vertically downward, the region under the vessel centered on the vessel can be properly searched.

(5) In the above embodiment, the wave transceivers 2*f*, 2*b*, 2*r*, and 2*l* successively transmitted ultrasonic waves at a specific period, but this is not the only option, and ultrasonic waves may instead be continuously transmitted from the wave transceivers 2*f*, 2*b*, 2*r*, and 2*l*.

Figure 12:
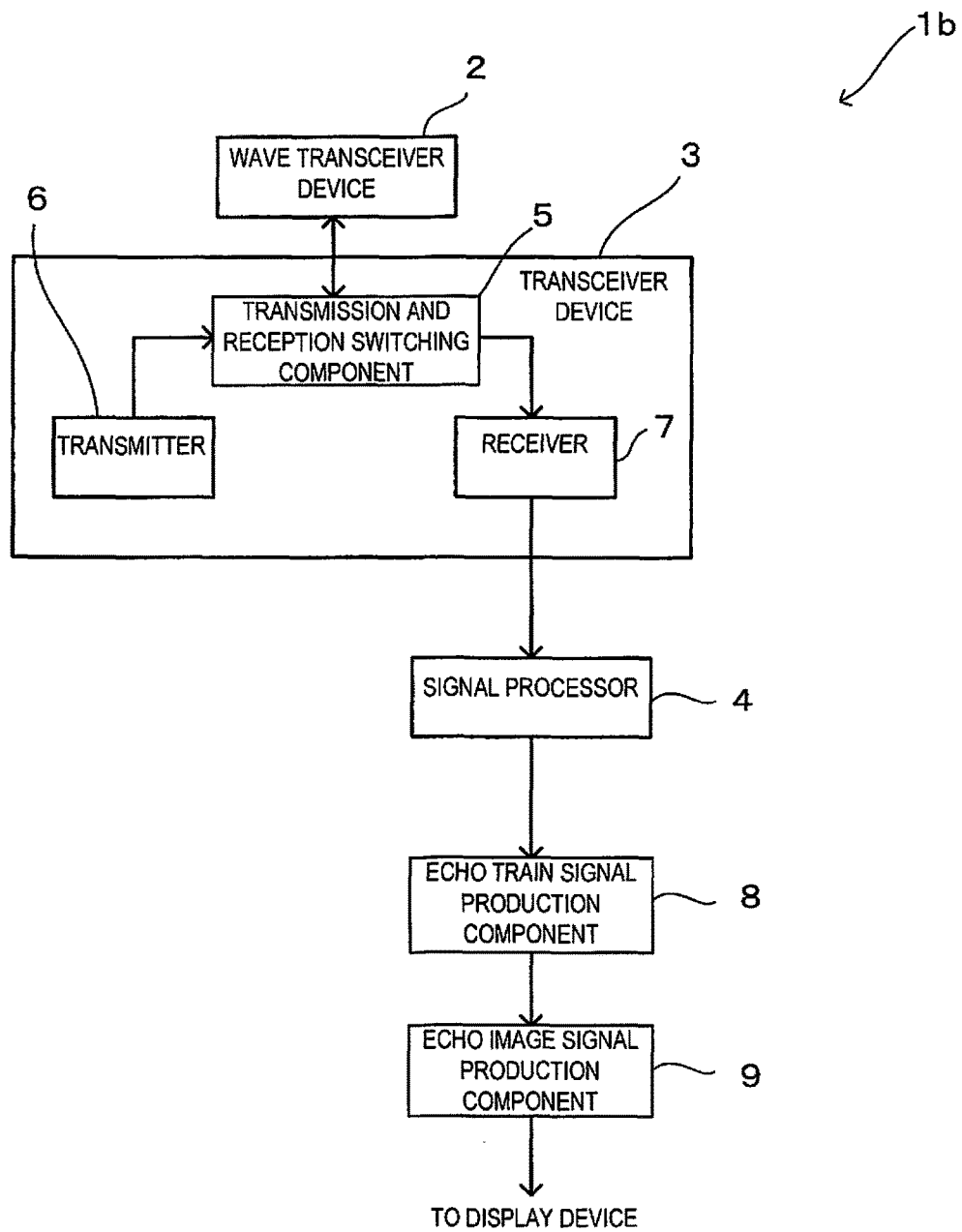
FIG. 12 is a block diagram of the configuration of an underwater detector pertaining to a modification example.

(6) FIG. 12 is a block diagram of the configuration of an underwater detector 1*b* pertaining to a modification example. The configuration of the underwater detector 1*b* in this modification example differs from that of the underwater detector 1 in the above embodiment in that the display device 10 is eliminated. With this modification example, echo image signals are outputted to a display device provided on the outside of the underwater detector 1*b* via a network or the like, and echo images are displayed on this display device.

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts.

While only a selected embodiment has been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A detection device comprising:
    a wave receiver disposed facing in a specific direction, and configured to periodically receive reflected waves corresponding to transmission wave transmitted from a wave transmitter; and
    processing circuitry configured to:
        produce an echo train signal from each of the reflected waves, the echo train signal comprising a series of samples sampled from the reflected waves, a position of a sample within the echo train signal relative to a starting point of the echo train signal being representative of a distance of the sample from the wave transmitter,
        produce an echo image signal based on each of the echo train signals in which each of the starting points is disposed at a same specific reference point, and
        rotate the echo image signal produced at that point in time in a peripheral direction about the reference point when a new echo train signal is produced.

2. The detection device according to claim 1, wherein
    the processing circuitry is configured to produce the echo image signal in which the echo train signals extend radially in mutually different directions in a state in which the starting point of each of the echo train signals is disposed at the same specific reference point.

3. The detection device according to claim 1, wherein
    the processing circuitry is configured to output the produced echo image signal to a display device that is configured to display an echo image produced based on the echo image signal.

4. The detection device according to claim 3, further comprising
    a plurality of the wave receivers, each reception beam formed by the wave receivers being oriented in mutually different directions,
    wherein the processing circuitry is configured to produce an echo train signal for each direction based on the reflected waves received by the plurality of the wave receivers, and produce a respective echo image signal based on each of the echo train signals for each direction in which each of the starting points for each direction is disposed at the same specific reference point, and
    on the display device, echo image for each direction produced based on the echo image signal for each direction is displayed on a plurality of split screens obtained by splitting a display screen of the display device.

5. The detection device according to claim 4, wherein
    the reference point is provided in a center portion of the display screen,
    the split screens are provided as regions between first and second line segments that extend from the reference point toward an outside of the display screen,
    positions of the split screens in the display screen correspond to directions of the reception beams respectively formed by the plurality of wave receivers, and
    echo train images produced based on echo train signals based on the reflected waves received by the respective wave receivers are displayed on the split screens corresponding to the respective wave receivers.

6. The detection device according to claim 5, wherein
    when the echo train signal is newly produced by the processing circuitry, the processing circuitry is configured to scroll the echo image displayed on the split screens at that point in time in a peripheral direction around the reference point from the first line segment side to the second line segment side, and configured to produce an echo image signal that displays at the first line segment side of the scrolled echo image an echo train image based on the newly produced echo train signal.

7. The detection device according to claim 5, wherein
    a third line segment that extends from the reference point toward the outside of the display screen is provided between the first line segment and the second line segment in each of the split screens, and when the echo train signal is newly produced by the processing circuitry, in the echo image displayed on the split screens at that point in time, the processing circuitry is configured to scroll the echo image between the first line segment and the third line segment in a peripheral direction around the reference point from the third line segment side to the first line segment side, configured to scroll the echo image between the second line segment and the third line segment in a peripheral direction around the reference point from the third line segment side to the second line segment side, and configured to produce an echo image signal that displays at the third line segment side of the scrolled echo image an echo train image based on the newly produced echo train signal.

8. The detection device according to claim 4, which is installed on a vessel and detects a target in the water, wherein the plurality of the wave receivers are attached to a hull bottom of the vessel, the reception beam of each wave receiver being oriented downward at an angle to a vertical direction.

9. The detection device according to claim 8, wherein the plurality of the wave receivers are attached to the hull bottom of the vessel, the reception beams of the wave receivers being oriented in a bow direction, a stern direction, a starboard direction, and a port direction of the vessel.

10. The detection device according to claim 9, further comprising said wave transmitter, having a transmission beam oriented downward.

11. The detection device according to claim 4, further comprising a plurality of said wave transmitters, each forming a transmission beam in a direction corresponding to the direction of the reception beam formed by each of the plurality of the wave receivers.

12. The detection device according to claim 11, further comprising a plurality of wave transceivers provided as the plurality of the wave transmitters and the plurality of the wave receivers.

13. The detection device according to claim 3, further comprising the display device.

14. The detection device according to claim 1, wherein the processing circuitry is configured to produce the echo image signal based on the new echo train signal and the rotated echo image signal.

15. The detection device according to claim 14, wherein the processing circuitry is configured to output the produced echo image signal to a display device that is configured to display an echo image produced based on the new echo train signal and the rotated echo image signal.

16. The detection device according to claim 1, further comprising a plurality of the wave receivers, each reception beam formed by the wave receivers being oriented in mutually different directions, wherein the processing circuitry is configured to produce an echo train signal for each direction based on the reflected waves received by the plurality of the wave receivers, and produce a respective echo image signal based on each of the echo train signals for each direction in which each of the starting points for each direction is disposed at the same specific reference point.

* * * * *